(12) United States Patent
Milunic et al.

(10) Patent No.: US 7,896,167 B2
(45) Date of Patent: Mar. 1, 2011

(54) BLOOD SEPARATOR AND METHOD OF SEPARATING A FLUID FRACTION FROM WHOLE BLOOD

(75) Inventors: David Milunic, Deptford, NJ (US); Donald Russell, Cherry Hill, NJ (US)

(73) Assignee: Akers Biosciences, Inc., Thorofare, NJ (US)

( * ) Notice: Subject to any disclaimer, the term of this patent is extended or adjusted under 35 U.S.C. 154(b) by 398 days.

(21) Appl. No.: 11/659,568

(22) PCT Filed: Aug. 5, 2005

(86) PCT No.: PCT/US2005/027822
§ 371 (c)(1),
(2), (4) Date: Jan. 15, 2008

(87) PCT Pub. No.: WO2006/017703
PCT Pub. Date: Feb. 16, 2006

(65) Prior Publication Data
US 2008/0210644 A1 Sep. 4, 2008

(51) Int. Cl.
*B01D 29/00* (2006.01)
*B01D 29/05* (2006.01)

(52) U.S. Cl. .................. 210/505; 210/483; 210/488; 210/489; 210/490; 210/491; 210/500.1; 210/503; 210/504; 210/506; 210/508; 422/101

(58) Field of Classification Search ............... 210/767, 210/800, 348, 483, 488, 489, 490, 491, 500.1, 210/503, 504, 505, 506, 508; 422/33, 73, 422/101, 60; 156/298
See application file for complete search history.

(56) References Cited

U.S. PATENT DOCUMENTS

| | | | | | |
|---|---|---|---|---|---|
| 3,249,491 | A | * | 5/1966 | Young et al. | 162/116 |
| 3,261,473 | A | * | 7/1966 | Riede | 210/282 |
| 3,262,578 | A | * | 7/1966 | Dennis | 210/489 |
| 4,216,280 | A | | 8/1980 | Kono et al. | |
| 4,293,378 | A | * | 10/1981 | Klein | 162/145 |
| 4,361,619 | A | * | 11/1982 | Forsten et al. | 442/35 |
| 4,477,575 | A | | 10/1984 | Vogel et al. | |

(Continued)

OTHER PUBLICATIONS

International Search Report for International Application No. PCT/US05/27822, (Jan. 2006).

*Primary Examiner*—John Kim
(74) *Attorney, Agent, or Firm*—Reed Smith LLP; William J. McNichol, Jr.

(57) ABSTRACT

A novel composite of glass fiber paper and reinforcing material that is useful for high speed manufacturing of devices comprising it is disclosed. The composite is formed by pressing into a glass fiber paper, having multimodal (at least bi-modal) composition, a hydrophilic reinforcing material. The composite has anisotropic separation properties that are particularly useful for preparing a fluid fraction from whole blood. The preferred glass fiber paper comprises glass fibers such that there are a plurality of short fibers (6) having large diameters and long fibers (2) with smaller diameters. The preferred glass fiber paper also exhibits partial ordering. There are many more of the long fibers (2) with smaller diameters than of the short fibers (6) having large diameters. Also disclosed are several blood separator device designs for efficiently separating the fluid fraction of blood from whole blood using the composite.

14 Claims, 7 Drawing Sheets

U.S. PATENT DOCUMENTS

| | | |
|---|---|---|
| 5,262,067 A | 11/1993 | Wilk et al. |
| 5,342,424 A * | 8/1994 | Pfeffer ........................ 65/450 |
| 5,435,970 A | 7/1995 | Mamenta et al. |
| 5,785,725 A * | 7/1998 | Cusick et al. ................. 55/382 |
| 5,916,521 A | 6/1999 | Bunce et al. |
| 6,555,489 B1 * | 4/2003 | Pfeffer ........................ 442/390 |

* cited by examiner

BLOOD SEPARATOR AND METHOD OF SEPARATING A FLUID FRACTION FROM WHOLE BLOOD

1 FIELD OF THE INVENTION

The present invention relates to a novel composition of matter which is a composite material comprising partially ordered glass fiber paper impregnated, on one side with a hydrophilic polyester material. Preferably, the hydrophilic material is non-woven. The present invention also relates to a blood separator for separating blood fluids, whether serum or plasma, from blood cells in a sample, such as a sample of blood. More particularly, the present invention relates to an improved blood separator that allows for rapid separation of the fluid fraction from cellular components in even very small volumes of blood samples.

2 BACKGROUND OF THE INVENTION

The separation of the fluid fraction, whether serum or plasma, from blood is of great importance in the clinic. Blood is made up of two fractions: blood cells, and the liquid in which they are suspended, blood plasma ("plasma"), a proteinaceous fluid. The important cell types encountered in blood are the red blood cells, the white blood cells and platelets although other cell types may be detected as well. Blood serum ("serum") is the fluid remaining after the removal of fibrin clots and cells.

Although whole blood is obtained relatively easily and in principle is capable of providing valuable information, its use is limited by problems in handling it for use in reliable rapid diagnostic assays. For example, if a diagnostic assay is based on a colorimetric reaction, hemolysis of red blood cells introduces errors. Even when the readings are not affected by colors contributed by hemolysis, the presence of cell lysates and its contribution variable recovery of the fluid fraction is a source of error. It is therefore desirable to reproducibly separate cellular components of whole blood to obtain a fluid fraction that can then be used in downstream applications.

The ability to measure a wide variety of physiologically active substances, both naturally occurring and synthetic, has assumed increasing importance as an adjunct to both diagnosis and therapy. While for the most part such assays require clinical laboratory determinations, there is an increasing awareness of the importance of being able to conduct assay determinations in a physician's office or in the home. These latter environments typically require that the assay have a simple protocol and be relatively free of sensitivity to small changes in the conditions under which the assay is carried out. Importantly, inaccurate measurements of reagents and sample should, whenever feasible, be avoided.

It is desirable that such devices and assays are fast, easy to use with few or no complicated procedures, readily readable, accurate and capable of being manufactured in mass quantities at a low cost (per unit). These goals usually require that the devices be amenable to manufacture using automation and be sufficiently robust for the handling required therefor.

The use of whole blood in the case of certain rapid diagnostic assays creates special problems. For example, if the diagnostic assay is based on a calorimetric reaction, turbid or colored solutions, such as from red blood cells, disturb the readings. It is therefore desirable to separate cellular components of whole blood to obtain the fluid fraction that can then be used in downstream applications. In particular, it is desirable to separate cellular components from the fluid fraction of whole blood in the absence of hemolysis because hemolysis causes components of red blood cells to be released into the fluid fraction and potentially interfere with downstream applications.

Attempts have been made to develop rapid diagnostics for the direct use of whole blood. For example, test papers coated with semi-permeable membranes to prevent the contact of larger components of the sample to contact the test paper have been developed (see, e.g., U.S. Pat. No. 3,092,465). Another example is the use of swellable films into which only the dissolved components of the blood, but not the erythrocytes, can penetrate (see Federal Republic of Germany Patent Specification No. 15 98 153). However, higher molecular weight components of the blood, for example lipids or substrates bound to serum proteins, for example bilirubin, cannot be determined in this way because they are also not able to penetrate into the film or to pass through the semi-permeable membrane. A disadvantage of certain filter systems is that blood penetrates through the membrane filter very slowly.

A conventional manner of separating the fluid fraction from erythrocytes is centrifuging. However, especially in the case of using small amounts of sample, such as 50 microliters or less, this gives rise to problems and the separation of supernatant and precipitated cellular components. Further, conventional methods require more handling time by the doctor, nurse, technician, or tester. Such additional handling is generally undesirable for efficiency as well as hygienic reasons. Moreover, in some point of care situations, a centrifuge may not be available.

Therefore, it is desirable to create a device to reduce the amount of handling required to separate blood fluids from cellular components of whole blood and, in particular, rapidly and effectively separate the fluid fraction from cellular components of small volumes of blood.

It is known that lymphocytes and leukocytes can be separated from blood when blood is filtered through a layer of synthetic resin fibers with an average fiber diameter of 5 to 20 micrometer in the case of separating lymphocytes, and of 3 to 10 micrometer in the case of separating leukocytes (see, e.g., Federal Republic of Germany Patent Specifications Nos. 29 08 721 and 29 08 722). However, since the erythrocytes can pass through the filter along with the plasma, these filters are not suitable for obtaining plasma because the erythrocytes can interfere with the downstream application, such as a calorimetric test.

Separators that separate the fluid fraction from blood cells are known in the art. The U.S. Pat. Nos. 4,477,575 and 4,816,224 issued to Vogel et al. on Oct. 16, 1984 and Mar. 28, 1989 respectively. ("the Vogel patents") were the first to disclose the use of glass fibers having density of 0.1 to 0.5 gm./ml with an average fiber diameter of 0.2 to 5 microns for separating the fluid fraction from blood.

Additional devices for separating the fluid fraction from whole blood that involve a glass fiber-based filtration mechanism are described, e.g., U.S. Pat. No. 4,696,797, issued Sep. 29, 1987, to Kelton. To facilitate the handling of small volumes of blood, e.g., 50 microliters or less, dye indicator systems as described, e.g., in U.S. Pat. No. 6,544,474, issued Apr. 8, 2003, to Douglas, were developed. Blood separation devices are described in U.S. Pat. No. 5,135,719, issued Aug. 4, 1992, to Hillman et al. that include a glass microfiber filter or filters with agglutinin for separating cellular components, e.g., erythrocytes, from the fluid fraction of whole blood. Agglutinin promotes the aggregation of blood cells and thereby improves the filtration process. The sole driving force for the movement of plasma from the filter to a downstream application is capillary force provided by a tubular capillary. A potential drawback of these glass fiber-based separators is that the separation of blood cells from whole blood often does not occur without hemolysis. Due to the hemolysis, certain components of erythrocytes contaminate the recovered fluid fraction, which may interfere with downstream applications.

In an effort to reduce hemolysis during the separation process, blood separators were developed with a layer of glass fibers, wherein the glass fibers are coated with, e.g., polyvinyl alcohol and/or wherein the layer contains an erythrocyte-aggregating substance. Such a device is described in U.S. Pat. No. 5,262,067, issued Nov. 16, 1993, to Wilk et al.

Certain improvements to the glass fiber-based separation method were described, e.g., in U.S. Pat. No. 5,435,970, issued Jul. 25, 1995, to Mamenta et al., which discloses devices for separating blood cells from biological fluids using a non-absorbent, porous unitary support, which can be made from glass fiber, and a blood cell binding composition, such as lectin. Similarly, U.S. Pat. No. 6,008,059, issued Dec. 28, 1999, to Schrier et al., describes the separation of the liquid portion of blood from the cellular components of whole blood using a pad of porous material. The pad of porous material is permeable to the liquid portion of blood but capable of trapping the cellular components of blood. The pad of porous material is further described as typically containing a binder for the cellular components of blood. The blood cell binding composition improves the effectiveness and efficiency of the blood separation process.

Many attempts for separating the fluid fraction from blood use multiple layers of filters and paths in attempts to permit flows around or past regions that have become clogged due to red blood cells. None of the known methods teach demonstrably gentle methods for trapping red blood cells in a region where the blood sample is applied with little to no migration of red-blood cells while the fluid fraction is separated efficiently.

U.S. Pat. No. 5,916,521 issued to Bunce et al. on Jun. 29, 1999 ("the '521 patent") discloses the use of a filter comprising sheet like capillary forms such that a first capillary form has a larger pore size for allowing some particulate matter to pass and is laterally connected to a second capillary form having a smaller pore size for trapping all particulate matter. Within each sheet, the pore sizes are substantially isotropic. The '521 patent also teaches lateral flow of blood to open pores if pores in a transverse path are blocked resulting in a progressively spreading region impregnated with red blood cells, both due to lateral flow within the filter and around the clogged pores at the site of application of blood.

In addition to glass fiber filters, polysulfone resins have also been used in blood separators. Polysulfone resins are extremely chemically resistant and also have some desirable mechanical properties. They, however, must be converted to a micro-porous structure, either in the form of a sheet stock or as fibers, to function as blood separators. Presently, two companies offer polysulfone based blood separators, namely Pall Corporation and Prime Care (Holland). These blood separators are in a sandwich form with separate collector pads. These separators also do not readily release the fluid fraction. In another aspect, polysulfone based materials also require multiple steps during manufacturing and are expensive compared to glass fiber papers.

U.S. Pat. No. 4,216,280, issued Aug. 5, 1980, to Kono et al. (the "Kono patent") discloses glass fiber paper based battery separator mediums and methods for making them from combinations of glass fibers having different diameters. The Kono patent also discloses battery separator mediums having, in addition to glass fibers, synthetic resin fibers such as polyester, polypropylene, or acrylonitrile fibers that are uniformly dispersed within the glass fibers. The Kono patent actually discloses making glass fiber papers that are suitable for retaining fluids as opposed to separating a fluid fraction from a whole blood sample.

In summary, the known art employs various combinations of pore-sizes, hydrophobic surfaces, glass fibers and the like in the quest for a device suitable for separation of the fluid fraction from blood. The known art teaches the use of thin fibers, typically having a diameter less than five microns and preferably around or below one micron. The methods also rely upon speedy removal of any recovered fluid fraction since red blood cells eventually reach and increasingly contaminate the recovered fluid fraction, both via direct contamination and due to hemolysis over time.

Significantly, the known methods and devices are not amenable to automation since, the most effective separation medium used therein, glass fibers, are brittle and difficult to handle. Thus cutting the material into specific and accurate shapes and packaging thereof, often requires significant amount of manual labor rather than automated handling.

3 SUMMARY OF THE INVENTION

A novel composite having a layered structure is disclosed along with a device based on it for preparing a fluid fraction from whole blood. The novel composite comprises a fibrous separation medium impregnated into one side with a reinforcing material. The fibrous separation medium is anisotropic. Without intending to be bound by theory, it presents a first pore size in a first direction and a smaller pore size in a second different direction. The impregnating reinforcing material also reduces the pore size in a portion of the fibrous separation medium due to compaction in the impregnated part of the fibrous separation medium upon pressing in of the reinforcing material. The reinforcing material is preferably a hydrophilic polyester material that is bonded to the fibrous separation medium with a hot melt adhesive. In a preferred embodiment the hydrophilic polyester material is non-woven and the preferred hot melt adhesive is an ethylene vinyl acetate based web.

The composite may further comprise a semi-permeable or impermeable film that reinforces the composite and increases its stiffness. The thickness of the semi-permeable or impermeable film may be selected to achieve a particular degree of stiffness. In an preferred embodiment of the present invention, such a composite may comprise a film that is about 1.5 mils thick, less than about 5 mils thick, about 8 mils thick, about 10 mils thick, about 11 mils thick, about 12 mils thick, about 13 mils thick, about 14 mils thick, about 15 mils thick, and at least about 16 mils thick. Preferably the film include a hot melt adhesive coating that comprises ethylene vinyl acetate. Example films are supplied by TRANSILWRAP COMPANY, INC. of Chicago, Ill., USA. This novel composite comprising this secondary reinforcement is stiffer and easier to machine for high-speed manufacturing. The secondary reinforcement may be carried out in a single step with the reinforcement of the fibrous separation medium with the reinforcing material or, alternatively, in a separate step.

Unlike the fibrous separation medium, which is preferably a glass fiber paper and, thus, quite frangible, the novel composite may be machined into various shapes including triangular, U, dumb-bell, T, and paddle shapes. Such machined pieces having dimensions as small as of the order of a few mm each, preferably about 40 mm or less, and even more preferably about 10 mm or less may be made using the novel composite and handled in automated manufacturing of devices comprising them.

In an embodiment of the present invention the fibrous separation medium comprises: fibrous material comprising a plurality of clusters of fibers having substantially aligned short large-diameter fibers and a plurality of clusters of fibers having substantially aligned long small-diameter fibers, wherein there are fewer of the short large-diameter fibers than the long small-diameter fibers; and a reinforcing material impregnating a bottom side of the fibrous material. Preferably, most of the long small-diameter fibers are, on an average, about twice (or more) as long as the short large-diameter fibers.

The relative thickness of the fibrous separation medium that is impregnated by the reinforcing material is preferably selected from the set consisting of at least about 1%, at least about 5%, about 10%, about 15%, about 20%, about 25%, about 30%, about 35%, about 40%, about 45%, about 50%, and less than about 55%. The reinforcing material may impregnate 15-60%, 35-60%, preferably 20-45%, and most preferably 25-35% of the glass fiber material.

In a preferred embodiment of the present invention, the fibrous separation medium comprises glass fibers and a binder, such as partially hydrolyzed polyvinyl acetate, with the binder present at a level not exceeding about 8%.

The long small-diameter fibers preferably have a length selected from the set consisting of about 6 mm, about 8 mm, about 10 mm, about 12 mm, about 14 mm, about 16 mm, about 18 mm, and at least about 20 mm, while the diameter is selected from the set consisting of at least about $3\mu$, about $4\mu$, about $5\mu$, about $6\mu$, about $7\mu$, and about $8\mu$ and the short large-diameter fibers have a length selected from the set consisting of about 5 mm, about 6 mm, about 7 mm, about 8 mm, and about 9 mm, while the diameter is selected from the set consisting of at least about $13\mu$, about $14\mu$, about $15\mu$, about $16\mu$, about $17\mu$, about $18\mu$, about $19\mu$, and at least about $20\mu$.

In a preferred embodiment, the long small-diameter fibers have a length of about 6-20 mm and a diameter of about $6\mu$, while the short large-diameter fibers have a length of about 6-8 mm and a diameter of about $17\mu$. Also, the proportion of the long small-diameter fibers to the short large-diameter fibers is about four to one. Further, the ratio of the diameters of the two types of fibers may be greater than two to one or even three to one. In a particularly preferred embodiment, the fibrous material is a battery separator glass fiber paper. Whatman and Co. battery separator paper Nos. F472-14, F472-11 and F472-9 are preferred.

The composite is, for example, useful in reproducibly producing a fluid fraction from whole blood with little to no hemolysis of erythrocytes. This production of the fluid fraction is rapid and typically obviates the need to centrifuge whole blood. Furthermore, the easily obtained fluid fractions in accordance with the invention enable measurement of the type or concentration of a blood component of interest in cheaper, convenient, yet accurate assays.

A preferred embodiment of the present invention encompasses a device for separation of the fluid fraction from blood, comprising a separation medium comprising a plurality of short large-diameter fibers and a plurality of long small-diameter fibers displaying partial order by way of similar orientation of fibers that are close together, the separation medium, preferably, being in the form of a layer such that, the plurality of short large-diameter fibers and the plurality of substantially aligned long small-diameter fibers in the layer are substantially coplanar and form a first size of pores suitable for migration into a plane, and a second size of pores suitable for migration along the plane, wherein there are fewer of the short large-diameter fibers than the long small-diameter fibers; and a reinforcing material impregnating one side of the separation medium with a hot-melt adhesive to form a composite material. Preferably, the composite further comprises a fluid impermeable backing laminated to the reinforcing material. The device may further comprise a proximal portion of the composite material for receiving blood; and a distal portion of the composite material for collecting the fluid fraction from blood. The reinforcing material preferably comprises hydrophilic polyester fibers.

The device may further comprise a proximal application port for applying whole blood and a distal collection port for collecting the fluid fraction. The present invention encompasses blood separation devices with more than one application and collection ports in a single device. The device may include a capillary or other means for collecting the fluid fraction. Such a means may be either integral with the device or as a component to be used for withdrawing the fluid fraction from the receiving port. For instance, in one embodiment of the present invention, a capillary may be removeably attached to the distal end of the composite to receive the fluid fraction as it is produced.

Surprisingly, lectin having affinity for red blood cells greatly enhances separation of fluid from blood. Hence, preferably, the device further comprises a lectin having affinity for blood cells. Suitable lectins include but are not limited to potato D lectin (from Solanum Tuberosum), Ulex Europaeous agglutinin (gorse lectin), and Phaseola Vulgaris agglutinin (kidney bean lectin). Potato D lectin is preferred.

A device using the composite may further comprise a collector pad abutting the distal portion, wherein the collector pad absorbs, but does not retain the fluid fraction. Moreover, a concave elastomeric cap may be placed over a proximal application port, whereby the fluid fraction is displaced by pneumatic pressure. Alternatively, the fluid fraction yield may be enhanced by eluting with a high density organic liquid that is immiscible with blood, plasma and serum.

In another aspect, the distal portion of the composite may be substantially shaped into a point defined by a cut angle selected from the set consisting of about 45°, about 40°, about 35°, about 30°, about 25°, about 50°, about 55°, and about 60°.

In a preferred embodiment a method for preparing a fluid fraction from whole blood comprises the steps of: applying the whole blood to a proximal application port on the composite of the present invention described previously herein followed by collecting a fluid fraction produced from it at a distal collection port. The fluid fraction may be collected directly from the composite, e.g., with a capillary or a pipette, or via a collection pad.

The method may further include additional steps to pump out the fluid fraction, such as a step selected from the set consisting of applying a pneumatic pressure and applying a high density organic liquid that is immiscible with the blood sample.

Another embodiment of the present invention encompasses a method for high-speed manufacturing of a device for separating a fluid fraction from a cell suspension by selecting a fibrous separation medium, impregnating a reinforcing material to a bottom side of the separation medium to form a composite; and shaping a distal portion of the composite into a point.

The manufacturing method may further comprise enclosing the composite in a casing such that the casing has a hole for applying the cell suspension for application at a proximal portion of the separation medium, and a second hole for withdrawing a substantially cell-free fluid fraction of the cell suspension. The manufacturing method may also comprise abutting a collector pad to the distal portion of the composite, wherein the collector pad absorbs, but does not retain the fluid fraction. The manufacturing method may also include fusing a capillary to a distal portion of the composite.

The manufacturing method may further comprise compressing the composite at a pinch point. Surprisingly, unlike conventional glass fiber paper, the composite advantageously prevents total closure of the pinch point under compression and permits fluid to pass while retaining red blood cells. There is a surprising lack of hemolysis at the pinch point.

An embodiment of the claimed invention encompasses a kit for separating a fluid fraction from a blood sample. The kit comprises: the composite of the present invention described herein, a casing for holding the composite, wherein the casing has openings suitable for applying a blood sample and for collecting a fluid fraction prepared from the blood sample. Further, the kit may include a collector pad abuttable to a distal portion of the composite, wherein the collector pad absorbs, but does not retain fluid. The kit may also include a capillary or a pipette with a bulb for collecting the fluid fraction. The kit may further comprise a breakable capsule for releasing an immiscible liquid at or near the pinch point to further increase the fluid fraction yield by displacing the fluid fraction from the composite.

In an aspect, a preferred blood separation device includes anisotropic separation means for facilitating flow and sequestration of cells in one preferred direction by providing a larger pore size while drawing away the fluid fraction in a direction different from the preferred direction by employing smaller pore sizes. The preferred device also includes reinforcing means impregnating the anisotropic separation means to make the anisotropic separation means easier to manipulate and process, e.g., into a point without crushing it.

In yet another aspect, the invention comprises a method for using a battery separator medium having at least bi-modal distribution of fiber lengths and diameters to prepare a fluid fraction from whole blood, wherein the battery separator medium is anisotropic in that it comprises a plurality of short large-diameter fibers and a plurality of long small-diameter fibers displaying partial order by way of similar orientation of fibers that are close together. The battery separator medium has fewer of the plurality of short large-diameter fibers than the plurality of long small-diameter fibers. The plurality of long small-diameter fibers are, on an average, twice or more in length than the plurality of short large-diameter fibers. Further, the battery separator medium has a first size of pores suitable for migration into it and a second size of pores suitable for migration along it. The method comprises applying a blood sample to the battery separator medium at a first point, and subsequently collecting a fluid fraction from a second point removed from the first point.

Without intending to be bound by theory, the preferred battery separator medium presents a first average path length to cellular material in blood that is substantially less than a second average path length presented to a fluid component of blood in a direction along the battery separator medium. Moreover, the fluid flow along the second average path is relatively shielded from the flow in the first path. Accordingly, the battery separator presents large pores that are capable of allowing the cellular material in blood to enter it. Since the fluid movement along the battery separator is shielded by the partially ordered long short diameter fibers, the red blood cells are not significantly exposed to shear forces from high velocity fluid flow.

The preferred novel composite and blood separator device based on it advantageously exhibit the following properties:
 1. separation of a fluid fraction from whole blood in five minutes or less for a full range of hematocrits;
 2. reproducible and stable demarcation between red blood cells and the fluid fraction without evidence of irregular flow or hemolysis discernable by eye;
 3. yielding a fluid fraction that is at least about 50%, more preferably at least about 60%, even more preferably about 70%, and most preferably about 80%, of the total available fluid volume in normal hematocrit blood;
 4. sufficiently stiff to be self-supporting;
 5. capable of producing a fluid fraction at a variety of compression levels;
 6. capable of producing a liquid fraction from a single drop of blood; and
 7. physically and mechanically ruggedness suited for high-speed automated manufacturing.

These and other features of the claimed invention are further described with the assistance of the following illustrative drawings and the detailed description.

4 BRIEF DESCRIPTION OF THE DRAWINGS

The present invention can be better understood by reference to the following drawings, wherein like references numerals represent like elements. The drawings are merely exemplary and the present invention is not limited to the embodiments shown.

5 DETAILED DESCRIPTION OF THE INVENTION

5.1 Composite:

In one aspect, the invention provides a novel composite comprising a fibrous separation medium impregnated with a reinforcing material. The reinforcing material is a hydrophilic polyester material. In a preferred embodiment the hydrophilic polyester material is non-woven.

According to one embodiment of the invention, the composite comprises a fibrous material with a multimodal distribution of fibers having a plurality of clusters having substantially aligned short large-diameter fibers and a plurality of clusters having substantially aligned long small-diameter fibers, wherein there are fewer of the short large-diameter fibers than the long small-diameter fibers; and a reinforcing material impregnating a bottom side of the fibrous material. Surprisingly, the present inventors have found that a family of products used as storage battery separators, e.g., those manufactured by the Whatman Company, including but not limited to Whatman glass fiber papers identified as F-472-14, F 472-11, and F-472-9.

The reinforcing material in the composite may be non-woven polyester fibers that are hydrophilic. According to an alternative embodiment of the invention, the composite is anisotropic in that it presents a first set of pores in one direction and a second set of pores in a second direction such that substantially more larger-formed elements can pass thorough the first set of pores than through the second set of pores.

Figure 1:
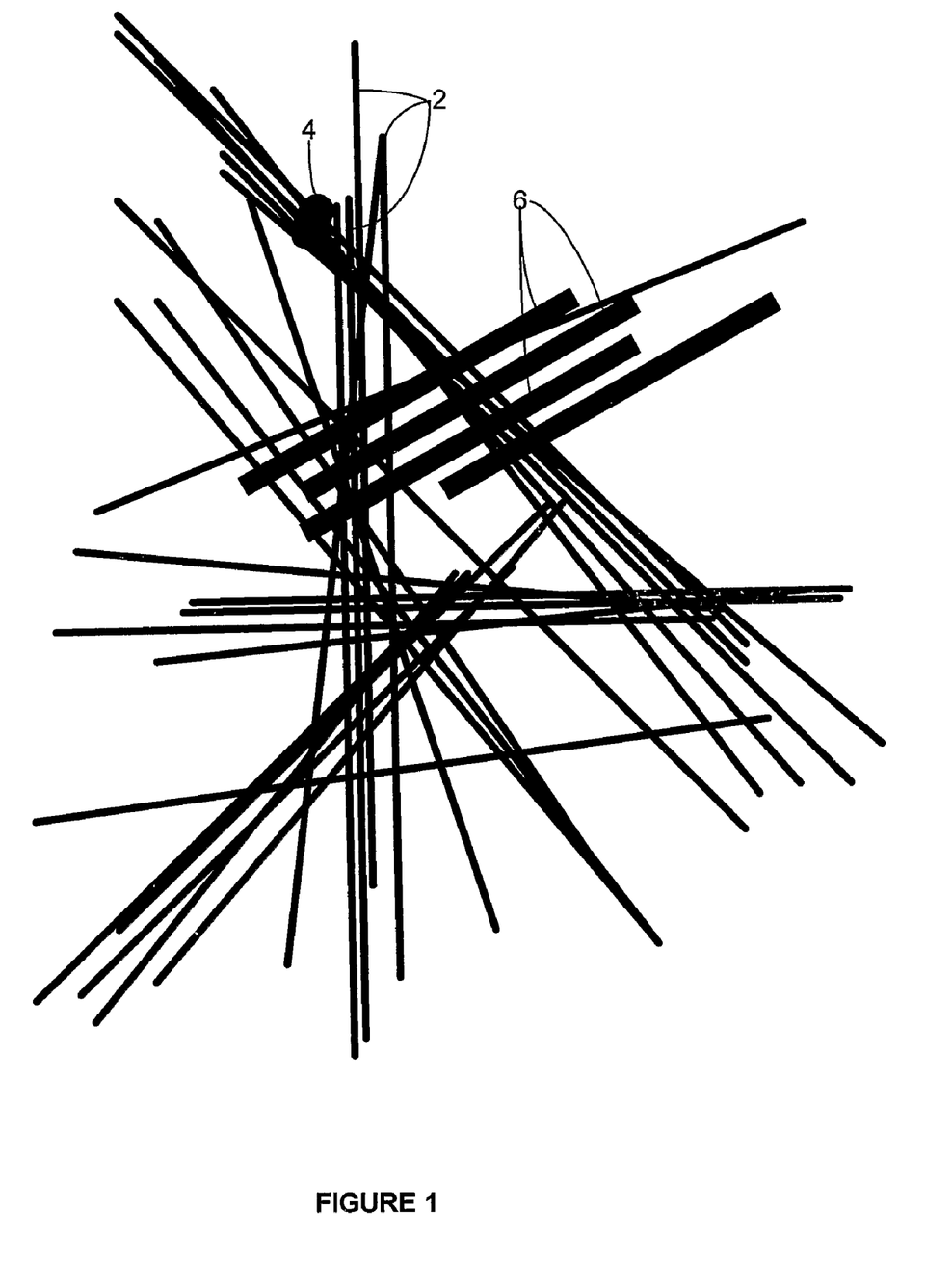
FIG. 1 shows an schematic of the arrangement of the glass fibers in the glass fiber paper.

The short large-diameter fibers and long small-diameter fibers in the fibrous material are glass fibers. In the Whatman papers discussed above, the glass fibers were found to be longer in length and diameter than those usually used in blood separators. Also the structure of the glass fiber paper showed substantial partial order rather than a completely random arrangement of glass fibers. This is illustrated in FIG. 1, which provides a schematic view of some of the glass fibers in an illustrative layer to show the partially ordered arrangement of glass fibers. Long short-diameter fibers 2 exhibiting partial order, along with binder 4 and a similar but more open cluster of short large-diameter fibers 6 is shown as substantially lying in a common plane.

Substantial partial order in this disclosure refers to the increased likelihood of similar orientation of fibers that are physically close together. For fibers that are relatively far apart, the orientation tends to become more random. The longer length of the short-diameter fibers is expected to lead to the formation of relatively long channels defined by fibers that are close together that may provide capillary action. Similar channels with a somewhat larger pore size and shorter extent may be formed by the large-diameter fibers as well.

The preferred glass fiber paper is multimodal, e.g., at least bimodal, in that it comprises predetermined fractions of glass fibers of different diameters and lengths. It preferably comprises glass fibers of at least two types of diameters and fiber lengths defining a bimodal paper. For instance, in one embodiment a first type of glass fibers have a length selected from the set consisting of about 6 mm, about 8 mm, about 10 mm, about 12 mm, about 14 mm, about 16 mm, about 18 mm, and at least about 20 mm, while the diameter is selected from the set consisting of at least about 5μ, about 6μ, about 7μ, and about 8μ. The second type of glass fibers have a length selected from the set consisting of about 5 mm, about 6 mm, about 7 mm, about 8 mm, and about 9 mm, while the diameter is selected from the set consisting of at least about 13μ, about 14μ, about 15μ, about 16μ, about 17μ, about 18μ, about 19μ, and at least about 20μ.

The Whatman battery separator glass fiber papers are also stronger due to the presence of glass fibers with larger diameters than the customary glass fiber papers taught to be preferable for separating the fluid fraction from blood. Preferable grades of glass fiber papers were examined under a comparator microscope and factors such as their layout, composition and the like estimated. A sample of such estimates is provided in TABLE 1.

TABLE 1

|  | Long small-diameter fibers | Short large-diameter fibers |
| --- | --- | --- |
| Fiber Diameters | 6μ | 17μ |
| Fiber Length | 6-20 mm | 6-8 mm |
| Binder - | 8% partially hydrolyzed polyvinyl acetate (estimated) | |

These glass fiber papers still benefited from reinforcement to make them suitable for handling during automated manufacturing. Some of the choices for reinforcing the glass fiber papers that were considered include:

a) Thermosetting resin—Epoxies, styrenated polyesters and acrylics were tested as coatings and as impregnants. The resulting products were strong but hard and brittle. Blood did not separate on these composites; and b) Polyvinyl acetate. This resin is often used in minor amounts to improve the strength of glass fiber paper. Although present in the glass fiber paper at low levels, increasing its level with the aim of significantly improving the strength of gave products that neither absorbed blood nor separated it.

The fibrous separation material is impregnated with a reinforcing material to form the novel composite of the invention. It was found that the Whatman battery separator glass paper could be commercially manufactured as a laminated glass fiber paper to form the composite 12 of FIG. 2. For lamination, a reinforcing material was pressed into the glass fiber paper such that it impregnated the glass fiber paper. Preferably, about 20 to 25% of the thickness of the glass fiber paper was impregnated by the reinforcing material. However, more or less of the fraction of the glass fiber paper may be impregnated by the reinforcing material. The fraction of glass fiber paper that is impregnated may be selected from the set consisting of at least about 1%, at least about 5%, about 10%, about 15%, about 20%, about 25%, about 30%, about 35%, about 40%, about 45%, about 50%, and less than about 55%.

Preferably, the lamination is carried out by placing a hot melt adhesive between the glass fiber paper and the reinforcing material. Upon pressing together the three layers and raising the temperature to about or above the melting temperature of the hot melt adhesive, the adhesive flows into both the reinforcing material and the glass fiber paper. Further, the glass fibers separate sufficiently to allow impregnation by the reinforcing material. Upon cooling the composite is formed as the hot melt adhesive sets.

The preferred hot melt adhesive is compounded ethylene vinyl acetate copolymer that is in the form of a web, e.g., the web adhesive PO90 made by BOSTIK FINDLEY Inc. of Huntington Valley, Pa., USA. The preferred hot melt adhesive has a softening point of about 97° C.

The preferred reinforcing material is non-woven hydrophilic polyester, e.g., REMAY™, which is manufactured by BBA Filtration, that is readily wet by blood. However, other hydrophilic fibrous materials that are compatible with impregnation into glass fiber paper may also be used.

Figure 2:
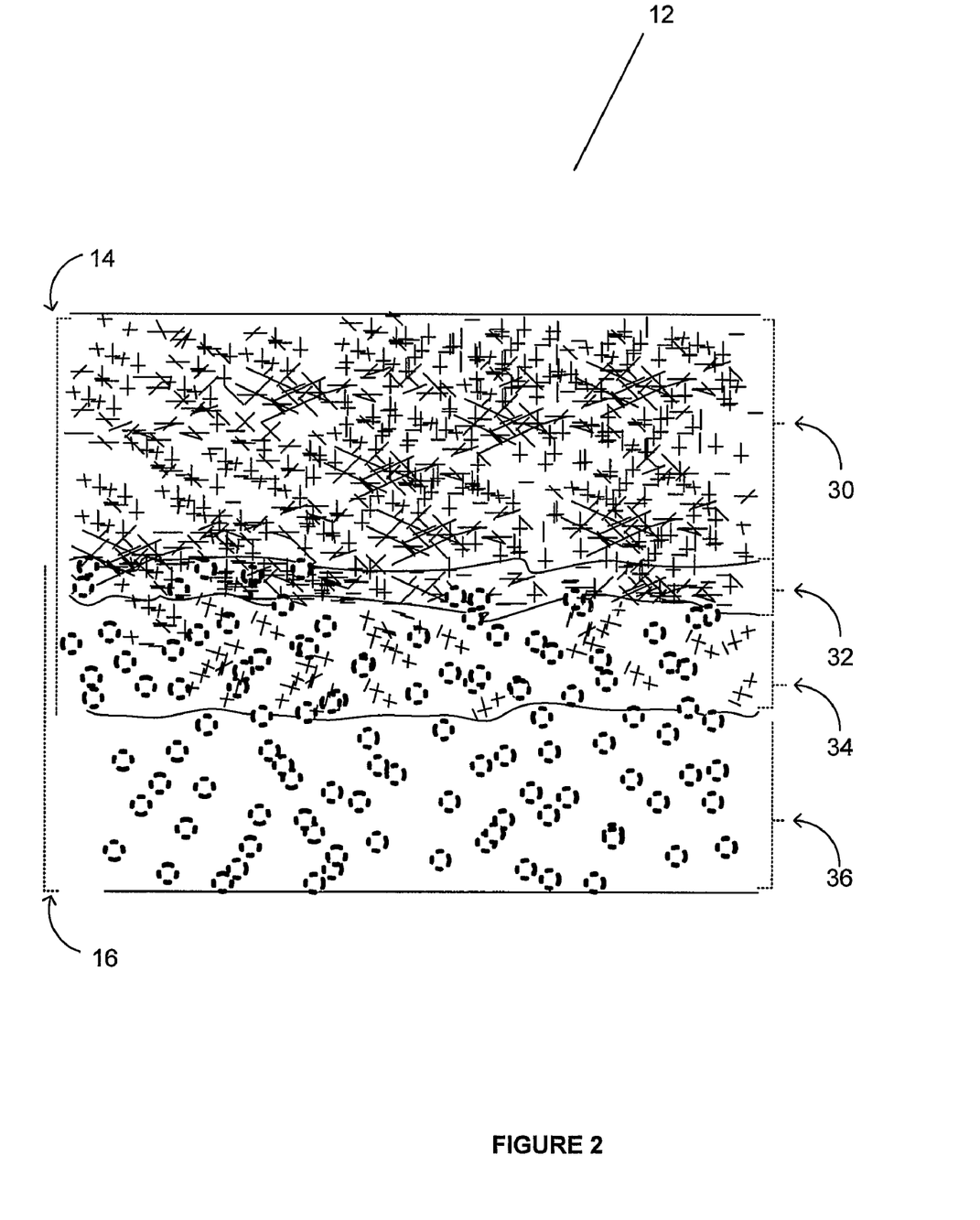
FIG. 2 illustrates a cross-section of the composite.

When the reinforcing material, e.g., REMAY™, is pressed into the glass fiber paper, the monofilaments in the reinforcing material displace and compress the glass at the interface as is shown in FIG. 2. Without intending to be limited, this forms an interfacial layer with increased capillarity. When a sample such as whole blood is applied to the non-reinforced face of the separator, there may be both a planar and transverse flow vector relative to the plane of the paper. The embedded impregnated portion of the non-woven hydrophilic polyester material forms walls around the non-compressed regions. This configuration may also increase capillary pressure. Under these conditions whole blood reaches the reinforced layer and initiates separation of the fluid fraction while the upper layer is absorbing and expanding. This theory may help explain the fluid fraction flowing ahead of red cells well before they reach their flow limit.

FIG. 2 shows an illustrative cross section through composite material 12 showing the state of separation medium 14 and reinforcing material 16 bonded to it. As shown, the microstructure of the composite has a top layer 30 comprising only of the separation medium followed by compression zone 32 in which the reinforcing material displaces and compresses glass fibers to give rise to a high capillarity interface. Below layer 32 is layer 34 with glass fibers in the interstitial spaces of the reinforcing material, followed by a reinforcing material layer 36.

The composite may provide additional benefits, such as improved structural integrity, i.e., is sufficient for cantilever mounting inside a housing. The composite can be bent 90-120° over ¼" diameter mandrel as compared to 10-20° for the non-reinforced grade. In certain embodiments, the composite may be mounted in housing reinforcement to attach or otherwise to couple glass fiber paper to housing. Glass fiber paper that is not reinforced may be too floppy to be permanently mounted in housing. For example, without sufficient structural integrity, glass filter paper could slip out of guide rails.

The composite of the present invention may be further reinforced by laminating on the free side of the reinforcing material a non- or semi-permeable layer using an adhesive. Surprisingly, the composite that is so reinforced provides increased mechanical strength without substantially compromising its properties that useful for separating a fluid fraction from blood.

Further, the structural integrity of the composite may prevent leak through of cellular components of blood. Without ensuring the structural integrity of the glass fiber paper, leakage of cells through the glass fiber paper can occur. The structural integrity of the composite helps to prevent leak through of cellular components.

An unexpected advantage of the reinforcement is its performance in certain elution systems. In such elution systems, the composite is mechanically pinched or squeezed at the red blood cell flow demarcation limit. Conventional glass fiber papers, when compressed or pinched, undergo 30-40% irrecoverable permanent set in which the very small fibers are crushed into the interface with porosity lost. The composite of the present invention retains at least some of its porosity on compression while the pore structure is reduced in size.

In another aspect, because of its well-known frangible nature, small pieces of glass fiber paper generally cannot be shaped to form a structurally stable apex or point. Such a triangular shape is possible with the composite of the invention even with pieces as small as 5 mm×20 mm. For instance, a composite piece that is about 5 mm wide may be cut and shaped as a point defined by a cut angle at the apex selected from the set consisting of about 45°, about 40°, about 35°, about 30°, about 25°, about 50°, about 55°, and about 60°.

The composite can be cut to define an apex or shapes other than triangular as well. In certain embodiments, the glass fiber paper may be cut in a geometrical shape other than triangular. In a specific embodiment, the composite that is a few mm wide is cut in a U-shape. Such U-shaped glass fiber papers could not be made with non-reinforced separators.

This composite has superior properties for separating the fluid fraction from small volumes of whole blood. The composite is useful in various applications such as an improved blood separator for efficiently fractionating a high quality fluid fraction from very small blood volumes without requiring extensive processing. Moreover, the composite is stronger than the fibrous separation medium and may be machined and handled in course of automated manufacturing of devices comprising it.

5.2 Blood Separator Device

In another aspect, the present invention provides a blood separator advantageously useful for separating the fluid fraction (either plasma or serum or a combination thereof) from a blood sample. The blood separator can be used to separate any size blood sample depending upon the size of the composite material used. In an particularly preferred embodiment, the separator is used to separate small blood samples, e.g., having a volume of the order of 50 µl.

The blood separator of the invention comprises:

1) a composite material, described herein, shaped to separate and direct the fluid fraction from whole blood; and 2) a casing for holding the shaped composite and having a proximal application port for applying whole blood and a distal collection port for collecting the fluid fraction.

The composite may be produced efficiently in the form of a roll following lamination of the reinforcing material to the fibrous material. As described elsewhere herein, this lamination may be advantageously carried out by using a web type adhesive layer interposed between the preferred glass fiber paper and the hydrophilic polyester reinforcing material. This composite material may be further reinforced to stiffen it by laminating to it a semi- or non-permeable membrane. The composite is then cut into the shapes desired in the blood separator. These shapes include, without limitation, triangular, U-shaped, dumb-bell shaped, T-shaped, and paddle shaped pieces.

The blood separator further comprises a holder or cover into which the composite is fitted. Additionally, the composite used in the separator may comprise an amount of lectin or other material such as an antibody specific to red blood cells, white blood cells or both, which retard the movement of such cells in the composite.

Preferred embodiments of the inventive devices are able to produce a fluid fraction from whole blood in 5 minutes for less for a full range of hematocrit values with little to no hemolysis. At least 50% of total available fluid fraction may be recovered by such devices. Further, the devices are scalable to handle different volumes of whole blood by using an appropriately sized composite.

FIGS. 3-6 provide a few illustrative examples of the fluid fraction producing devices formed in accordance with the principles of the present invention. Similar components are identified by the same reference numbers for clarity and ease of comparison between the various figures.

The exemplary blood separation devices of FIGS. 3-6 are not exhaustive and the device design admits of many variations, including different geometries in which the novel composite may be used in shapes other than as a flat layer. For instance, it may be shaped so that part of the composite is horizontal, e.g., for application of the whole blood sample, and is continuous with another part that is vertical. Such a design may take advantage of gravity in harvesting the fluid fraction. Such variations will be readily apparent to one having ordinary skill in the art.

Alternative designs for the blood separator of the present invention also encompass sealed separation blood devices that may use, for instance, 100 µl of whole blood to prepare a fluid fraction. This fluid fraction, in whole or in part, may be further used in one or more assays within the device.

The typical blood separator designed to prepare a fluid fraction from a drop of blood may be about 70 to 80 mm long, with about the first 25 mm of its length infiltrated with red blood cells. A drop of blood may have a volume of about 40 µl to 60 µl, and may be treated as having an average of about 50 µl. Often a clamp is placed at or after 25 mm from the site of application of the blood sample such that while fluid may pass through, little or no cells pass by the clamped region. The clamp position is also termed the pinch point with a compression of about 30 to 40% of the thickness being applied. The cell blocking effect of the clamp is aided by the progressive formation of fibrin network and that further entraps red blood cells. However, if the clamp is placed too close to the site of application of the blood sample, there is increased hemolysis and the possibility of red blood cells infiltrating the fluid fraction.

In one embodiment of the invention, an ampoule filled with an immiscible liquid may be placed immediately beyond the pinch point. This ampoule is broken after the separation of the fluid fraction from blood to release the liquid therein and push the fluid fraction separated from blood to increase the fluid yield. The clamp prevents backflow or contamination by red blood cells. The use of such an ampoule is particularly useful in preparing a fluid fraction from high hematocrit blood samples.

In another aspect, the use of the composite of the present invention described herein, reduces the distance at which a clamp may be placed without increasing hemolysis or red blood cell infiltration. For instance, the clamp may be placed at about 20 mm. 21 mm, 22 mm, 23 mm or 24 mm from the site of application of the blood sample. This is due to the more effective trapping of red blood cells by the composite of the present invention, as is described in illustrative example 1 later in this disclosure.

Figure 3:
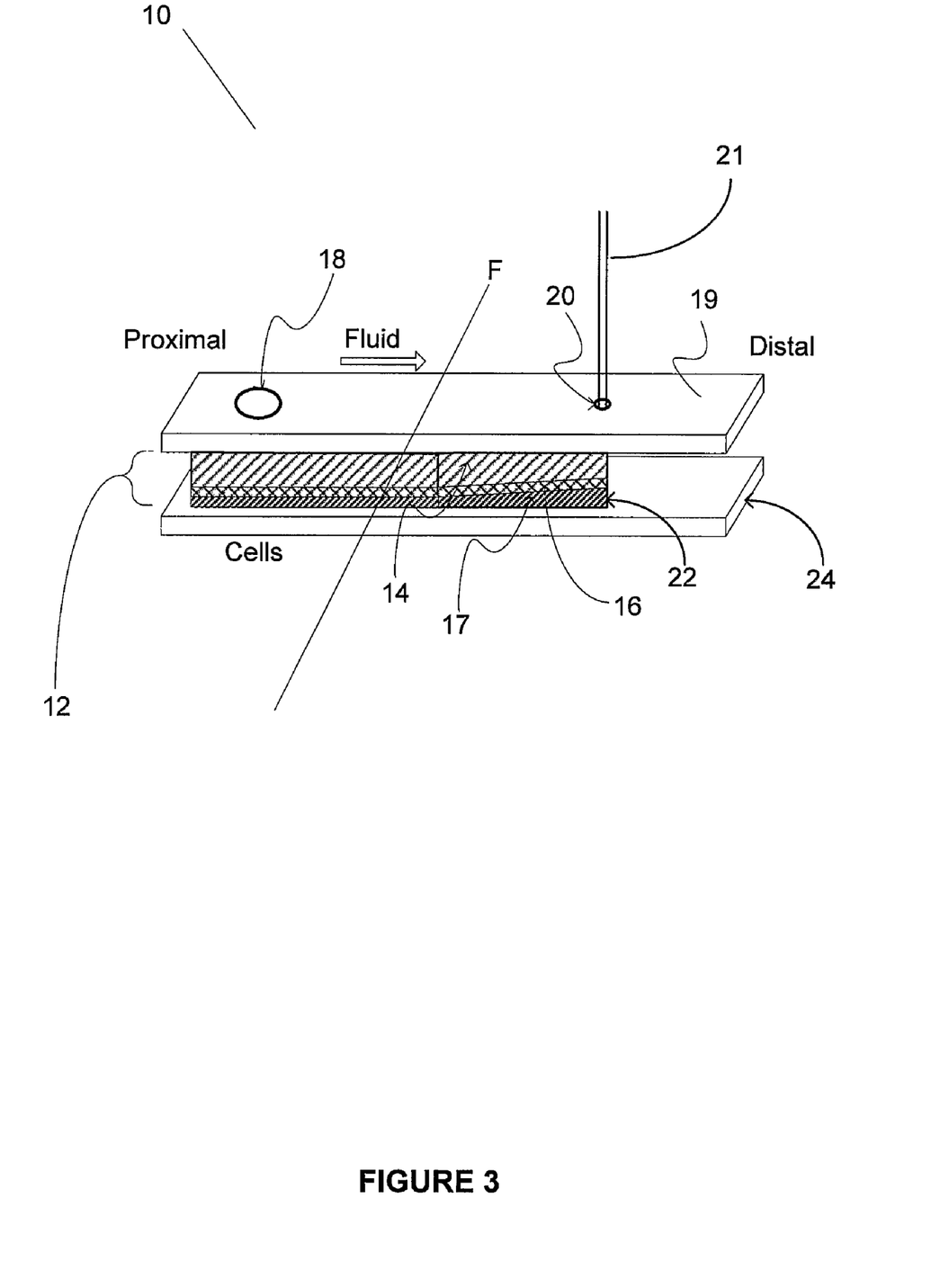
FIG. 3 shows a schematic view of a blood separator device of the present invention with only the top and bottom layers of its cover to show its components, and a capillary attached to the composite via a hole in the top casing.

In FIG. 3 is shown device for producing a fluid fraction from blood formed in accordance with the principles of the present invention, i.e., blood separator 10. Only the top and bottom layers of the casing of blood separator 10 are shown to schematically reveal its components. Blood separator 10 includes composite 12 comprising separation medium 14, impregnated by reinforcing material 16, a fluid impermeable backing 17, which is attached to composite 12 or may even be a part of composite 12, proximal application port 18 for applying whole blood, and distal collection port 20 for collecting a fluid fraction. As illustrated, proximal application port 18 is larger in diameter than distal recovery port 20. However, this is only an illustrative example and the ports may be the same or any combination of sizes.

There is an experimentally determined lateral flow distance beyond which red cells should not pass. At about this distance, or slightly earlier, a thin compressive line is clamped across the composite at the Pinch Point to further prevent migration of red blood cells beyond it. In blood separators of FIGS. 3-6, the Pinch Point position is indicated by the dashed line labeled 'F.'

The distal end of the composite is preferably shaped into a point, i.e., apex 22 in FIG. 3, although multiple points or other shapes may be used in alternative embodiments. The triangular shape of apex 22 at the distal end of composite 12 particularly facilitates the collection of the fluid fraction from one point using the collection device. Preferably, the cut angle defining the apex is selected from the set consisting of about 45°, about 40°, about 35°, about 30°, about 25°, about 50°, about 55°, and about 60°. Using prior art glass filters, which lacked such a triangular shape, the fluid fraction generally has to be collected from a larger area using a wicking mechanism.

Figure 6:
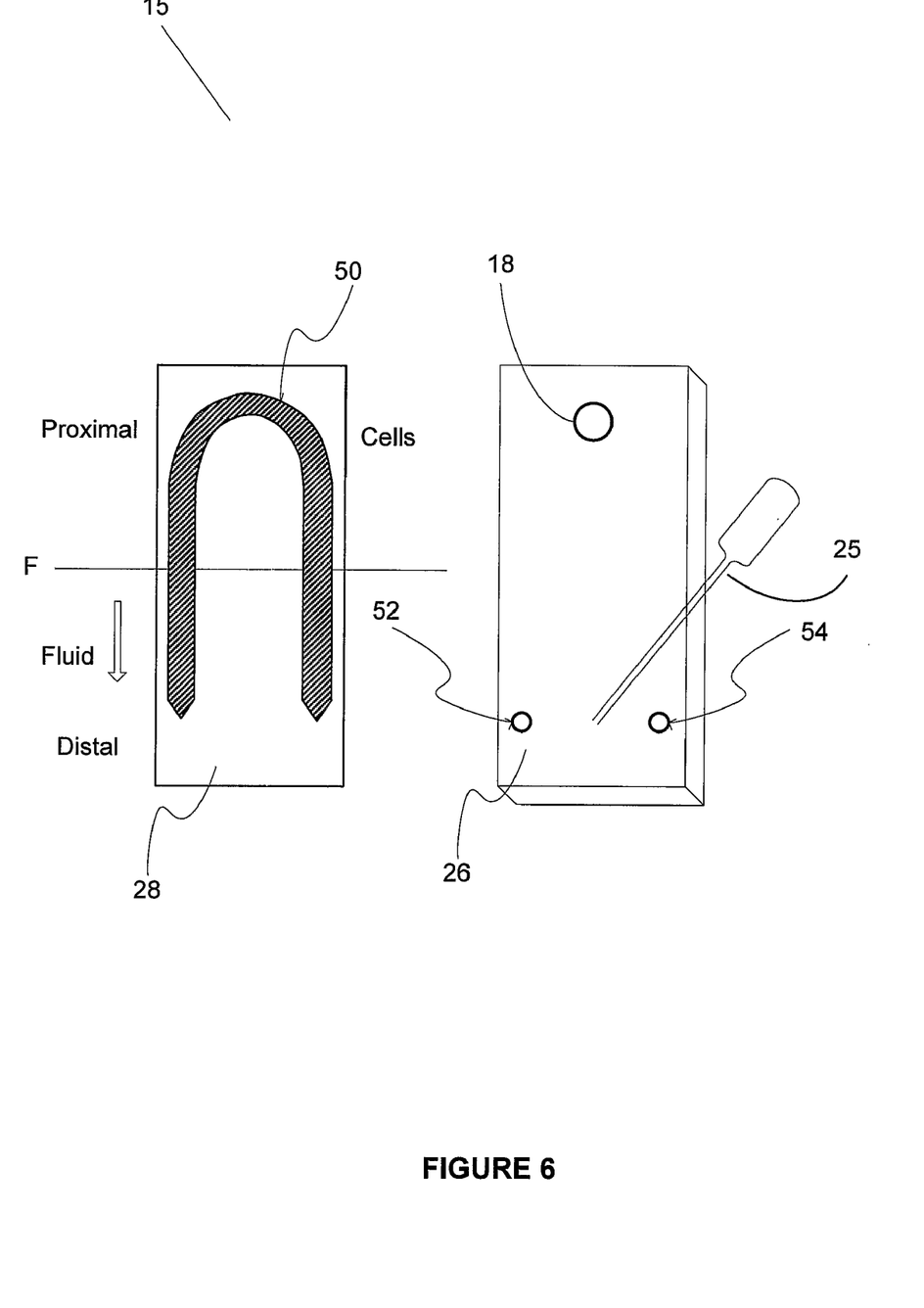
FIG. 6 shows a top view of blood separation device of the present invention that has been taken apart to show a composite having a U-shape.

In one embodiment, the composite may be cut in a geometrical shape other than triangular. For instance, FIG. 6 illustrates composite 50 having a U-shape such that distal end has two triangularly shaped points at which the fluid fraction can be collected via ports 52 and 54. Such U-shaped composites, and composites having other shapes, having a dimension of about 40 mm or less could not be made with non-reinforced separators known in the prior art. The novel composite described herein is suitable for shapes having dimension of the order of 10 mm or less.

Reinforcing material in composite 50 may be attached to an impermeable or semi-permeable layer, for instance by lamination, to further stiffen composite 50. which is placed on or attached to base piece 24. TABLE 2 lists the preferred constituents in a preferred embodiment of the invention.

TABLE 2

| Component | Example Source | Product Description |
| --- | --- | --- |
| Glass fiber paper | Whatman and Co. | Grade 472-14; alternatives include grades 472-9 and 472-11 |
| Reinforcing material | Remay made by BBA Non Woven | 3121N, Alternatives include 3201N, 7503, 3201N, Starevels 2253C, Remay 2003, 2004, 2015, 2006, 2010 |
| Non-Woven Adhesives | Bostik Co. Delnet Co. | PO90.20; Alternatives include PO 90.60 and PO90; each of which is spun-bonded non-woven web of ethylene vinyl acetate copolymers; X 450N, which is a reticulated film of ethylene vinyl acetate copolymers; |
| Lectins | Aldrich | Solanum tuberosum Potato D Lectin, which has affinity for N-acetyl β D-glucosamine oligomers; Alternatives include Ulex europaeous agglutinin; and Phaseola vulgaris agglutinin |

In one embodiment, the reinforcement material is estimated to be impregnated about 20-25% inside the glass fiber material and that portion of the glass fiber paper, in the embedment zone, will have a higher degree of compaction and smaller pores than unreinforced portion. This combination of the reinforcing material impregnating the separation medium results in rapid fixation of the red cells from whole blood coupled with high the fluid fraction yields.

The reinforcing material may impregnate 15-60%, 35-60%, preferably 20-45%, and most preferably 25-35% of the glass fiber material. Impregnation beyond about 40% of the glass fiber material may result in undesirable rupturing of some localized glass fibers.

The reinforcing material surface that is not in contact with the glass fiber material is preferably reinforced by laminating thereto a semi-permeable membrane (or a fluid impermeable membrane) that does not significantly penetrate into the reinforcing material. This stiffer material is desirable for deploying the composite in a cantilevered structure. Notably, this additional reinforcement does not significantly impair the performance of the composite, for instance, due to trapped air pockets.

A sample of blood applied to proximal application port 18 is drained of its fluid content as the cells suspended in blood are substantially retained in composite 12 at the site of application, which may be due to the larger pore sizes facilitating settling in and possible potato lectin or other alternative coatings that promote binding of the red blood cells to the coated fibers. Movement of cells along the plane of the composite may be prevented, e.g., by the mostly smaller pores in that direction in the region as well as the impregnated glass fibers and clot formation promoting glass fibers.

In an aspect, the glass fiber paper in composite 12 may be impregnated with an agent for binding red blood cells, such as a lectin or even suitable antibodies or other compositions. The use of lectin both enhances wetting and red blood cell immobilization rate. Although the novel composite of the invention possessed desirable separation properties, the separation rate could be increased by impregnation of the composite with potato lectin. The addition lectin increased the fluid fraction yields and ease of expression of the fluid fraction from the separator.

Various lectins are suitable for use in devices in accordance with the invention. Potato D lectin in a 8.5 PH buffer (HEPES, CA Cl2 2H2O, Na N3) is used in a preferred embodiment. The preferred lectin concentration range is about 10-50 micrograms/ml, and the preferred amount is about 10 micrograms/ml. It is impregnated into the reinforced glass fiber paper and then dried in place. The finished laminate is estimated to have about 0.3-0.6 micrograms of lectin/mm$^2$ or about 50 mg/ft$^2$ of substrate. Alternative immobilizing agents can be similarly used and the conditions for their use determined without undue experimentation by one having ordinary skill in the art.

Since the glass fibers are large there is no possibility for dense packing, and hence an open structure exists in glass fiber paper 14. Under swelling pressure the already open structure may become even more open and further decrease any flow restrictions on the fluid fraction.

The effect of the lectin in improving serum separation was evaluated by applying whole blood to the F472-14 (the preferred glass fiber paper from Whatman). The F472-14 absorbed 50 μl of whole blood in about 10 seconds, but no separation of the fluid fraction occurred for about 30 seconds after the red blood cell flow limit line was established, an additional 50-60 seconds were needed to complete the flow of the fluid fraction.

Surprisingly, Lectin treated composite of the present invention, based on the F472-14 glass fiber paper exhibited superior properties compared to either the composite alone or the F472-14 glass fiber paper. The lectin treated composite absorbed the applied whole blood in about five (5) seconds followed by separation of the fluid fraction in about 60 seconds compared to about 180 seconds for the composite lacking the lectin. The volume of the fluid fraction was greater with the lectin impregnated composite than with either the composite or the F472-14 glass fiber paper alone. The results of comparing the lectin coated composite to a number of different materials for preparing the fluid fraction from blood are summarized in TABLE 4 presented later in the illustrative Examples.

Various device designs for the production of the fluid fraction are possible. A preferred model illustrated in FIGS. 5 and 6 consists of two rectangular shell like pieces, a top 26 and a bottom piece 28, that are coupled to encase the composite within. In the bottom piece, the blood separator rests on a pedestal whose dimensions are the same as the separator width. It is preferably positioned between two guide pins to prevent lateral motion. When top piece 26 of the container is snapped into place it presses on the proximal end of the composite 12 and puts it into in a cantilevered mode.

Figure 5:
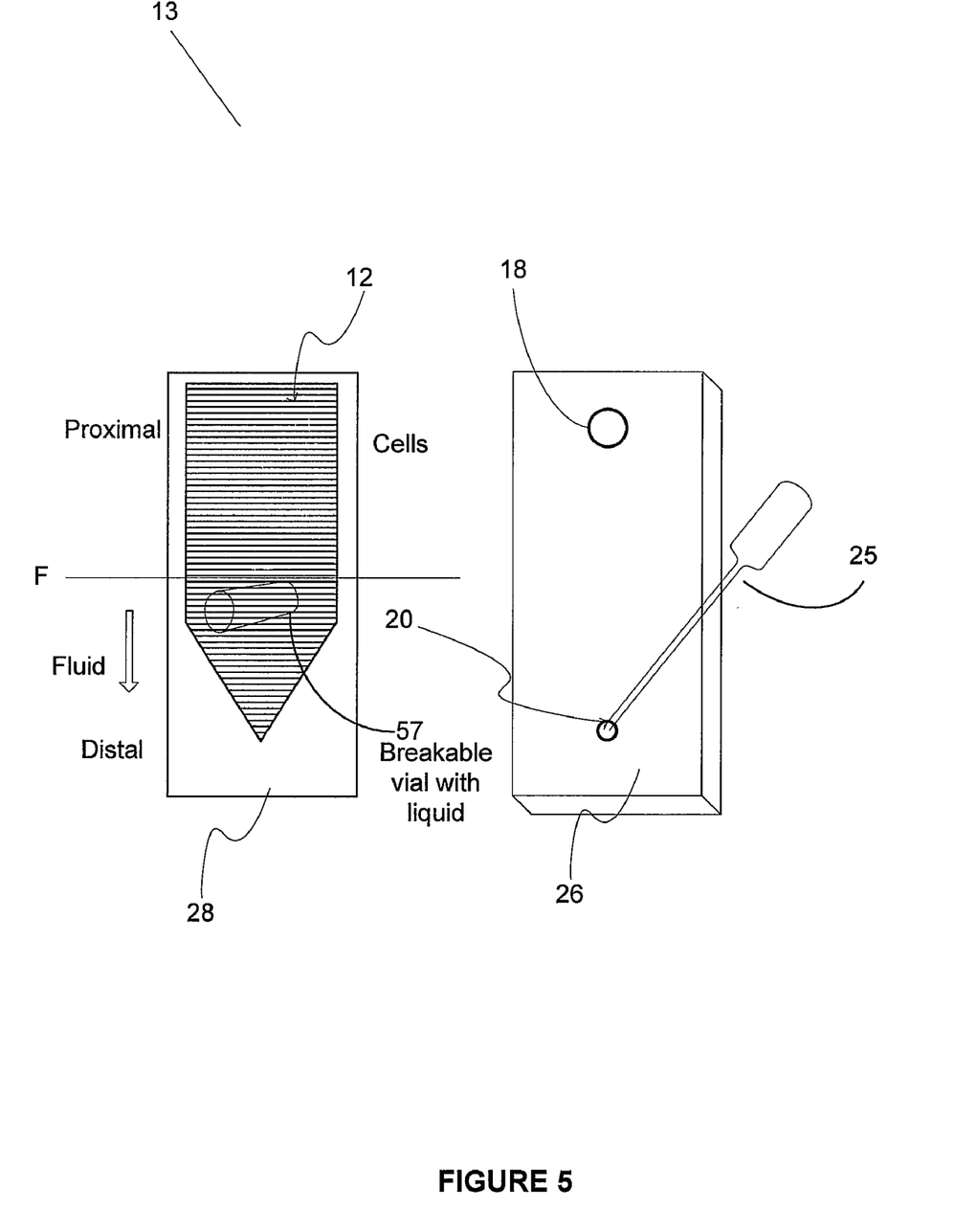
FIG. 5 shows a top view of blood separation device of the present invention that has been taken apart to show the upper and lower casing parts and the pinch point position.

The top piece has two holes in it to provide:
(1) blood entry port, i.e., proximal application port 18; and
(2) a port suitable for, for instance, inserting a capillary locator and holder, i.e., distal collection port 20. The blood entry port is over the proximal end of composite 12.

The fluid fraction output from the same blood volume may be increased by increasing the pressure head on the blood. In accordance with fluid mechanics, liquid pressure (head pressure) increases in proportion to the height of a column. In a flowing system the pressure is maintained for a longer period of time if it is fed by a liquid reservoir. Head pressure increase may be obtained by increasing the height from which the blood must flow to reach the separator. This is accomplished in the preferred embodiment by, for instance, deploying a length to diameter ratio of four to one or greater, even more preferably of 10 to one, and most preferably of 30 to one at the proximal application port 18. The greater head pressure on the blood is transmitted to composite 20 and pushes the liquid phase to the distal end of the separator where it accumulates. In another approach, proximal application port 18 has a larger diameter than the distal collection port 20 to enhance recovery of the fluid fraction.

Figure 4:
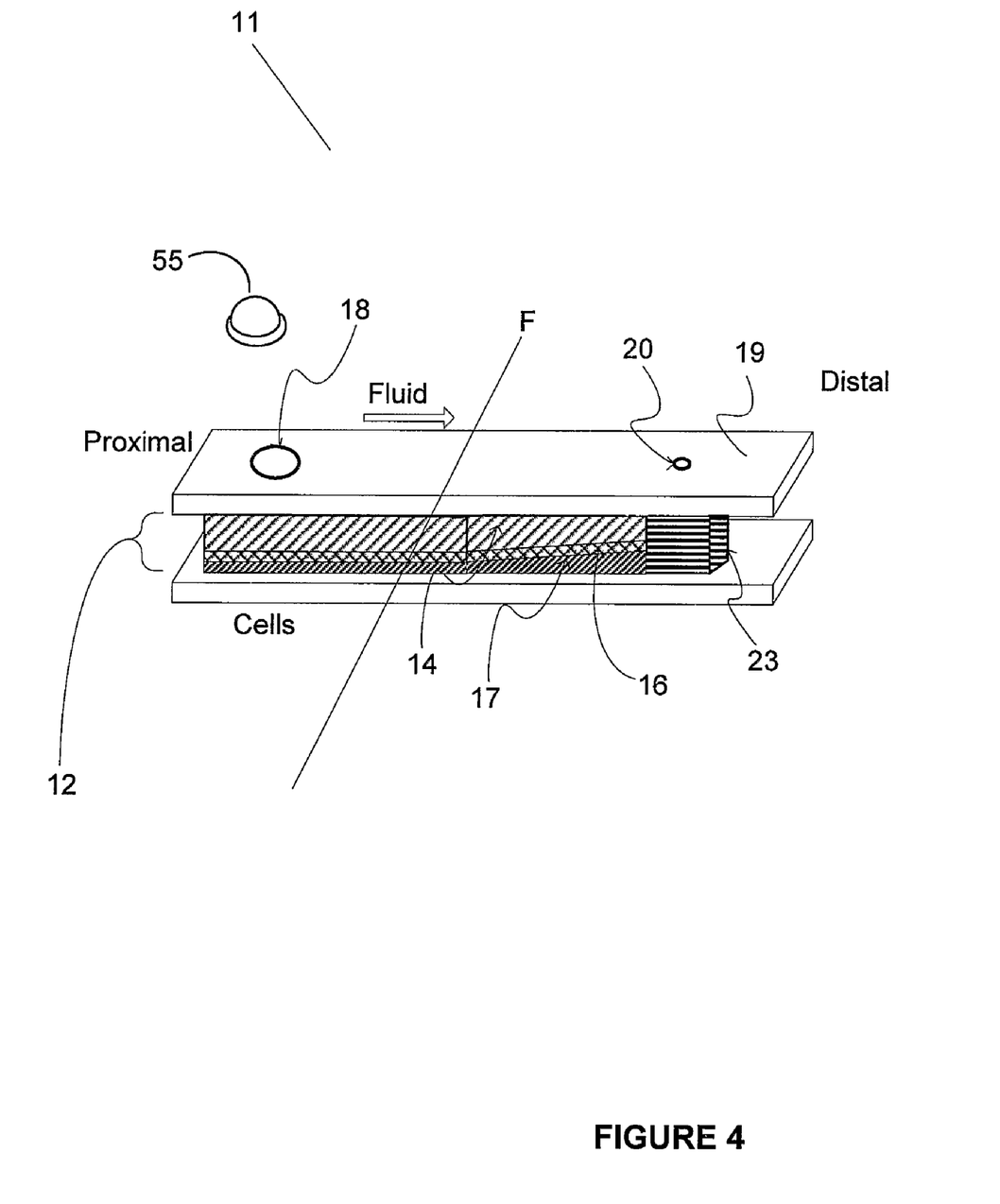
FIG. 4 shows a schematic view of a blood separation device according to the present invention with only the top and bottom layers of its cover to show its components, and a collector for receiving the fluid fraction.

Distal collection port 20 in the cover is located slightly beyond apex point 22 of the distal end of composite 12. A glass capillary fits snuggly into this hole and is positioned vertically to almost abut the distal end. As the fluid fraction is produced, the capillary is close enough to absorb it and fill up. A variation on this, illustrated in FIG. 4, places the distal end of composite 12 in contact with transfer piece 23 in blood separator 11. The capillarity of transfer piece 23 pulls the fluid fraction into itself. By selecting transfer materials that absorb, but then drain the produced fluid fraction, it is possible to accumulate the fluid fraction in a sump under the transfer material. A glass capillary may then be put either through the collector (vertical mount) or under it (horizontal mount). FIG. 4 also shows elastomeric cap 55, which may be placed over proximal application port 18 to apply a pressure.

As opposed to collection of the fluid fraction from glass fiber-based devices of the prior art where a wicking mechanism or capillary forces had to be employed to obtain the fluid fraction from the filter, in accordance with one aspect of the present invention, the fluid fraction can be obtained directly from the composite. Capillary-like channels create the force to move the fluid fraction through composite. Consequently, the fluid fraction can be collected at a collection region at distal end directly without the need for a wicking device.

Alternative to other collection mechanisms or optionally in addition to other collection mechanisms, composite can be squeezed to obtain the fluid fraction directly in liquid form. In certain specific embodiments, composite is mounted inside a flexible housing such that it can be squeezed by compressing the flexible housing, and the fluid fraction is obtained through an opening in the flexible housing. Compressing of the glass fiber-based filters of the prior art to obtain the fluid fraction would generally cause hemolysis. The improved composite of the present invention allows for its compression without causing unacceptable hemolysis. Without intending to be bound by theory, this lack of hemolysis may reflect the low shear forces directly experienced by red blood cells.

In certain embodiments, the fluid fraction can be delivered to some other carrier, e.g., via apex 22. A capillary may be contacted with the collection region at distal end of the composite, to collect and to transport the fluid fraction to another site (such as for testing). Optionally, a capillary is mounted inside a housing a support a such that the capillary a impinges on collection region of composite 12 to collect the fluid fraction, without necessarily removing it from the housing. Mounting the capillary inside the housing ensures that the contact between collection region of the glass fiber paper and the capillary is maximized. Also because both the capillary and the composite are mounted on the housing, they cannot move relative to each other and consistent collection of the fluid fraction from collection region of the composite is ensured. The capillary may located adjacent to second opening in the housing to allow removal of the fluid fraction.

In one embodiment, illustrated in FIG. 3, employs capillary 21 to collect the fluid fraction from composite 12. Capillary 21 is shown attached to composite 12, although this is not a requirement. FIGS. 5 and 6 show blood separators 13 and 15 with a capillary-bulb combination 25, that is not integrally connected to composite 12.

In certain embodiments, the collection device may be introduced through the second opening, described above, to collect the fluid fraction from the capillary. Alternatively, the collection device may be introduced through the second opening such that the collection device impinges on the apex of the composite to collect the fluid fraction.

Figure 7:
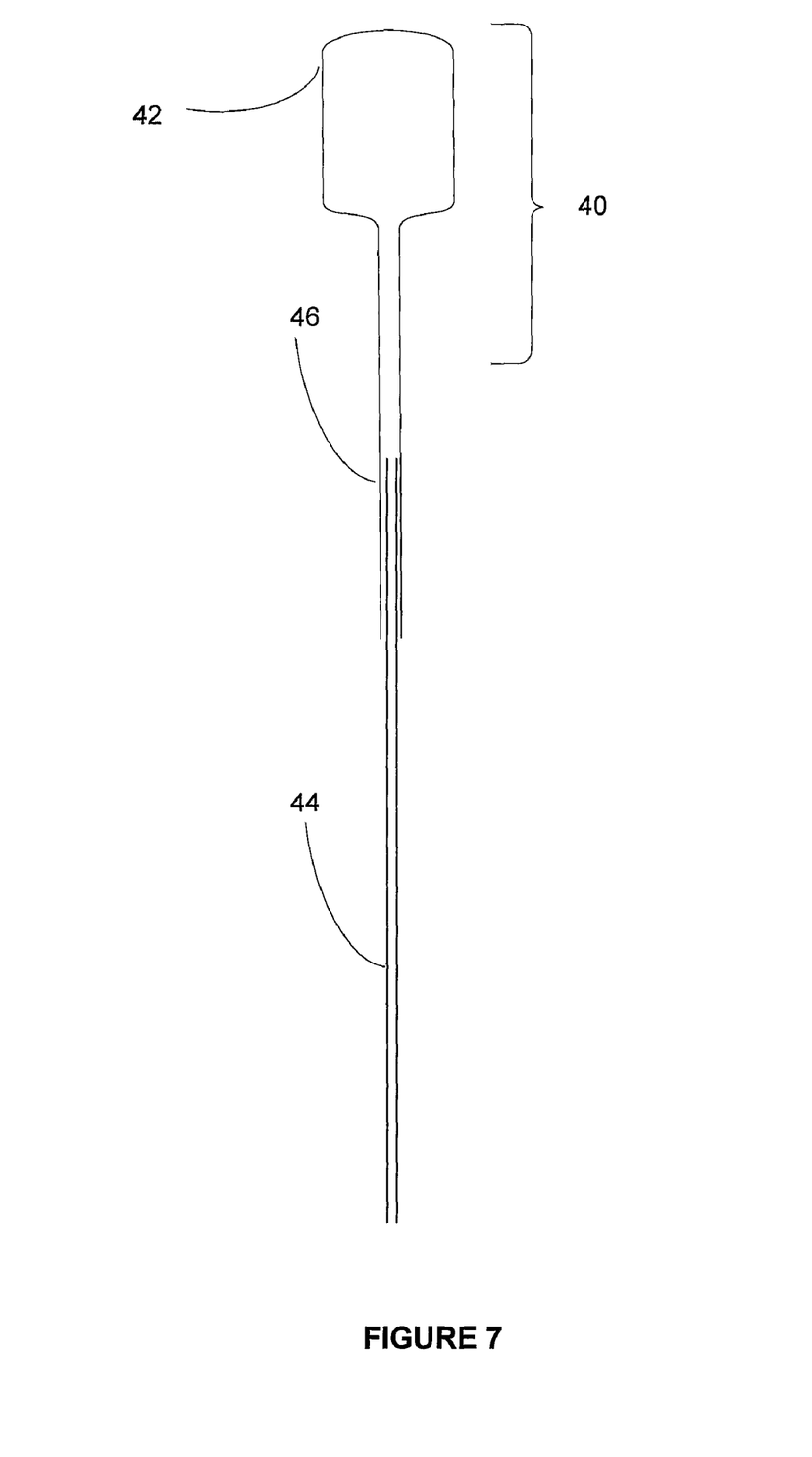
FIG. 7 shows a capillary pipette that may be used to collect a fluid fraction from a blood separation device.

An exemplary capillary pipette formed in accordance with the principles of the present invention is shown in FIG. 7. Capillary pipette 40 includes a pipette bulb 42 attached to a pipette tube 44 such that the internal space of pipette bulb 42 and the internal space of the pipette tube 44 are connected to each other. Capillary pipette 40 further comprises a capillary tube 46 which is at least in part preferably attached to pipette tube 44 via a seal.

In certain embodiments, the seal can be at any position between the inner wall of the pipette tube and the outer wall of the capillary tube. The seal fulfills two functions: (i) to physically attach capillary tube 46 to pipette tube 44; and (ii) to seal the inner space such that upon compression of pipette bulb 42, any liquid in capillary tube 46 is expelled. Because of the seal, air from the inner space can only be expelled through the capillary tube.

In certain specific embodiments, the capillary tube and the pipette tube are made from glass, and the pipette bulb is made from plastic (e.g., polyethylene). In certain other specific embodiments, the capillary tube, the pipette tube, and pipette bulb are made from plastic (e.g., polyethylene).

In certain aspects of the invention, the capillary pipette is calibrated such that a specified volume can be taken up by the capillary pipette and subsequently expelled. The volume depends on the amount of fluid needed for the downstream application. Calibration can be achieved by adjusting the total volume of the inner spaces such that only a defined volume of fluid can be taken up by the capillary. As the capillary is filled and displaces air from inside the capillary into the inner spaces, pressure builds up. At an equilibrium point, the pressure inside the inner spaces is equal to the capillary force inside the capillary tube and no more liquid is taken up by the capillary tube. Thus, the capillary pipette of the invention can be calibrated to take up a defined volume of liquid by adjusting the volume of the inner spaces. Alternatively, the capillary pipette can be calibrated by choosing the volume of the capillary tube such that a defined volume can be taken up by the capillary tube if the capillary tube 88 is fully filled. If the capillary pipette is calibrated in such a manner then the total volume of the inner spaces must be large enough for the capillary tube to be filled completely. Fluid fraction volumes as little as 0.2 microliters can be collected and transferred to downstream applications using the capillary pipette. Various size capillary tubes can be used to isolate the desired quantities of the fluid fraction. The capillary pipette preferably collects a portion of the produced fluid fraction from a point of collection in the housing and is automatically filled. The capillary pipette can be calibrated. If the capillary pipette is calibrated, the capillary pipette automatically fills to the required volume.

In certain embodiments, the capillary pipette may be mounted into the housing such that the capillary tube impinges on the collection region of the composite. If the blood separator has an apex, as described above, then the capillary pipette preferably impinges on the apex. In certain, more specific, embodiments, the capillary pipette may be removed from the composite. For example, the capillary pipette may be mounted into the housing such that it can be broken off such that the capillary pipette is removed from the composite thereby allowing the fluid fraction to be expelled from the capillary pipette. Mounting the capillary pipette into the housing ensures maximum contact between collection region of the composite and the capillary tube of the capillary pipette. Further, mounting the capillary pipette into the housing increases the reproducibility of yield of the fluid fraction that is collected. Because the composite and the capillary pipette are mounted into the housing such that they cannot move relative to each other, the position of the contact point between the capillary tube and the composite remains constant. Thus, by avoiding variable contact between the capillary tube and the composite the quantity is more likely to remain the same among different collection events. The advantage of reproducible yield is that the collected the composite can be directly used for a downstream application that requires a specific amount of the fluid fraction. In an exemplary embodiment, the collected the composite, whether the fluid fraction, can be directly used for a quantitative or semi-quantitative measurement of an analyte in the fluid fraction.

Without being bound by theory, when whole blood is applied, the fluid fraction separates and the red blood cells try to flow through the pinch point. There is a damming effect which permits fluid egress, but retains red cells. As the separation is completed, the red cells in the pinch point may solidify. When the fluid fraction is eluted, the red blood cells remain immobilized and no back-washing occurs.

6 EXAMPLES

6.1.1 Example 1 Blood Separator

Procedure: Strips of blood separator, prepared as described in Section 5, about 7 mm wide and about 70 mm long were each dipped to a depth of about 2 mm in a container holding about 20 ml of serum. One end of the strip was dipped into the serum and the time for a capillary rise of about 2 cm measured. The strip was removed and the time and distance determined for movement of the imbibed blood fluid. Comparative tests were conducted to evaluate the fluid fraction production by the composite and the preferred embodiment.

In another aspect, the results also show the effect of adding an agent for binding red blood cells to the composite. The glass fiber paper used as the fibrous material in the preferred embodiment of the composite of the present invention is the F472-14 glass fiber paper from the family of battery separator papers manufactured by Whatman Corporation. F472-14 paper alone, or as a part a composite made by laminating a polyester reinforcing material to F472-14, or with laminated composite further impregnated with potato D lectin were tested for their ability to separate a fluid fraction from blood. As is seen, the lectin impregnated composite of the invention superior properties.

Data showing relative rate of serum absorption and then the rate and distance of lateral capillary flow of the imbibed serum is presented in TABLE 3 below, wherein the composite is as described herein:

TABLE 3

| Product | Absorption (mm$^2$) | Max flow distance (mm) | Time (secs) | Estimated Serum Yield |
|---|---|---|---|---|
| Whatman GF-D[1] | 10 | 10 | 170 | 1 |
| Whatman GF-DVA[1] | 45 | 0 | — | 0 |
| Pall, Hema SepV[2] | 54 | 5 | 118 | 0.9 |

TABLE 3-continued

| Product | Absorption (mm²) | Max flow distance (mm) | Time (secs) | Estimated Serum Yield |
|---|---|---|---|---|
| Pall, Hema Sep L[2] | 37 | 5 | 143 | 0.14 |
| HV 5211AO[3] | 20 | 8 | 108 | 0.4 |
| Whatman Plasma Sep[4] | 80 | 10 | 196 | 0.125 |
| Whatman 472-I4[5] | 12 | 10 | 41 | 0.83 |
| Composite[6] | 12 | 20 | 180 | 1.7 |
| Lectin Impregnated Composite[7] | 5 | 25 | 60 | 5 |
| S & S24[8] | 7 | 0 | — | 0 |

[1]The glass fiber paper manufactured by Whatman that retains 98% of particles having a dimension of about 2.7 microns
[2]Microporous polysulfone sheet based separation devices that are assembled to have the vertical ('V') part, for sample application, connected to the lateral ('L') part, for separating the fluid fraction
[3]HV = Hollingsworth and Vose glass fiber filters with pore sizes of less than about a micron
[4]An experimental separator that is not based on the 472-14 battery separator paper
[5]A battery separator glass fiber paper made by Whatman, which is also preferred for making the composite of the present invention
[6]A composite made by reinforcing the Whatman 472-14 battery separator with a hydrophilic polyester reinforcing material
[7]The composite of the present invention including potato D lectin and a tracking dye, which composite exhibited a flow rate of about 338 µl in 5 seconds by rapidly absorbing the blood sample
[8]S & S = Schleicher & Scheull glass fiber filters with pore sizes of less than or about a micron

6.1.2 Example 2 Red Cell Capture by Separation Medium

Procedure: Each tested separator material was cut into 3"×3" pieces. One drop of whole blood was placed in the center of each separator and the following parameters were measured
(a) the initial diameter of the drop;
(b) the diameter after absorption;
(c) the time of absorption, which is a function of the rate of wetting by blood; and
(d) the distance to which serum migrates (measured from a ring surrounding the initial blood drop).

Before and after diameters indicate the extent of red blood cells' immobilization over time.

Results: The composite of a preferred embodiment of the invention absorbs the applied blood rapidly with little spreading of red blood cells beyond the area of initial application. The strikingly small changes in the drop diameter in the composite indicates that red cell immobilization occurs essentially as the blood is absorbed. Using the ratio of RBC flow distance to the serum flow distance (in mm) as the measure of the estimated serum yield, alternative separation media exhibited serum yields of less than half of that of the preferred lectin impregnated composite.

The data is presented below in TABLE 4.

TABLE 4

| Separator Material | Drop Diameter (mm) | | Absorption | Serum Ring |
| | Initial (mm) | Final (mm) | Time (secs) | Distance (mm) |
|---|---|---|---|---|
| Composite[1] | 7 | 7.2 | 15 | 14.2 |
| Plasma Sep[2] | 7 | 21 | 35 | 4 |
| Hema Sep V[3] | 10 | 20 | 60 | 5 |
| Hema Sep L[3] | 10 | 23 | 60 | 5 |
| GF-F[4] | 7 | 16 | 180 | 4 |
| GF-D[5] | 7 | 18 | 60 | 4 |
| GF-DVA[6] | 7 | 13 | 60 | 7 |

[1]A composite made by reinforcing the Whatman 472-14 battery separator with a hydrophilic polyester reinforcing material.
[2]An experimental separator that is not based on the 472-14 battery separator paper.
[3]Microporous polysulfone sheet based separation devices that are assembled to have the vertical ('V') part, for sample application. connected to the lateral ('L') part, for separating the fluid fraction.
[4]Glass fiber paper manufactured by Whatman that retains 98% of particles having a dimension of about 0.7 microns.
[5]Glass fiber paper manufactured by Whatman that retains 98% of particles having a dimension of about 2.7 microns
[6]Another grade of glass fiber paper manufactured by Whatman

6.1.3 Example 3 Measurement of Lithium Levels in Serum

Lithium is effective as a drug in some disorders, e.g., manic depressive illness. Lithium is unusual in that its effective levels are only slightly less than the toxic levels. Since compliance is an issue with many subjects prescribed the drug, rapid and accurate assays are needed to ensure proper drug delivery.

The Lithium Testing System disclosed herein is a rapid (about two (2) minute test) and suitable for a doctor's office or for use at a point of treatment. The Lithium testing system has three components:

(a) A blood cell separator for providing a precise microvolume of serum from whole blood;
(b) A Lithium Reagent, which is a substituted porphyrin compound that is highly specific for and very sensitive to the presence of Lithium; and
(c) A photometric reader, e.g., the InstaRead™ that is accurate at 505 nm.

A typical pack for the :Lithium System has 24 reagent filled cuvettes, with corresponding blood separators, bulb pipettes, blood collection tubes, lancets, alcohol swabs, adhesive bandages, gauze pads, patient record labels, an insert with instructions and a calibration kit that is sufficient for about 30 days performance.

In an exemplary application, in order to measure lithium levels, a few drops of blood are obtained from a subject, e.g., using a lancet. From a couple of drops of whole blood, a blood fluid fraction is prepared using the claimed blood separator device. A precise amount of the fluid fraction so obtained is introduced to a predetermined amount of the Lithium Reagent. Absorbance at 505 nm measured and used to estimate the concentration of lithium since the absorbance at 505 nm is linearly proportional to the concentration of lithium from about 0.0 to about 2.5 mEq/L of lithium.

The fluid fraction obtained using the claimed blood separator is sufficiently accurate and free from hemolysis that it is comparable to the standard, but more cumbersome and elaborate methods for preparing suitable fluid fractions, e.g., the centrifugation method (Vitros Lithium System K934106), for analyzing whole blood even for a critical substance like lithium. As noted previously, due to the risk of toxicity, it is important to accurately estimate the levels of lithium, and thus only reliable fluid fraction (of blood) preparation methods can be used.

A preferred model for the blood separator, which is used in a lithium detector assay based on detecting lithium levels in the fluid fraction from blood, consists of two rectangular shell like pieces, a top and a bottom piece, that snap together and encase the composite within.

Although the preceding description of the invention is in the context of the embodiments described herein, this is not intended to be a limitation on the scope of the invention. As readily recognized by one of ordinary skill in the art, the disclosed invention encompasses the disclosed embodiments along with other embodiments having many different configurations for providing multiple fluid fractions from cell suspensions such as whole blood and the like.

We claim:

1. A device for separation of fluid from blood, the device comprising:
    a separation medium comprising a plurality of short large-diameter fibers comprising a diameter of from about 13 microns to about 20 microns, and a length of about from 5 mm to 9 mm and a plurality of long small-diameter fibers comprising a diameter of from about 5 microns to about 8 microns, and a length of from about 6 mm to about 20 mm displaying partial order by way of similar orientation of fibers that are close together, the separation medium being in the form of a layer such that, the plurality of short large-diameter fibers and the plurality of substantially aligned long small-diameter fibers in the layer are substantially coplanar and form a first size of pores suitable for migration into a plane and a second size of pores suitable for migration in a direction substantially along the plane, wherein there are fewer of the short large-diameter fibers than the long small-diameter fibers;
    a reinforcing material impregnating a bottom side of the separation medium to form a composite, wherein a hot melt adhesive couples the reinforcing material to the separation medium;
    a proximal portion of the separation medium for receiving blood; and
    a distal portion of the separation medium for providing fluid from blood.

2. The device of claim 1, wherein the reinforcing material comprises polyester fibers suitable for impregnation.

3. The device of claim 1, wherein the reinforcing material further comprises a backing selected from the set consisting of a fluid impermeable material and a semi-permeable web.

4. The device of claim 1, wherein the composite further comprises a lectin to enhance binding of red blood cells to the composite.

5. The device of claim 1, wherein the composite is anisotropic in that it presents a first set of pores in one direction and a second set of pores in a second direction such that substantially more red blood cells can pass thorough the first set of pores than through the second set of pores.

6. The device of claim 1, wherein the short large-diameter fibers and the long small-diameter fibers are glass fibers.

7. The device of claim 6, wherein the ratio of the long small-diameter fibers to the short large-diameter fibers is selected from the group consisting of at least about four to one, about three to one, and about two to one.

8. The device of claim 6, wherein a binder binds the glass fibers.

9. The device of claim 8, wherein the binder comprises hydrolyzed polyvinyl acetate in an amount less than about 8% by weight of the glass fibers.

10. The device of claim 1, wherein the distal portion is substantially shaped as a point defined by a cut angle selected from the set consisting of about 45°, about 40°, about 35°, about 30°, about 25°, about 50°, about 55°, and about 60°.

11. The device of claim 1 further comprising at least one member of the set consisting of a collector pad abutting the distal portion, wherein the collector pad absorbs, but does not retain fluid.

12. The device of claim 1 further comprising a capillary attached to the composite.

13. The device of claim 1 further comprising a concave elastomeric cap over a proximal application port, whereby fluid is pumped out by pneumatic pressure.

14. The device of claim 1 further comprising a high density organic liquid that is immiscible with blood, plasma and serum.

* * * * *